United States Patent [19]

Schmiechen et al.

[11] 4,193,926
[45] Mar. 18, 1980

[54] 4-(POLYALKOXY PHENYL)-2-PYRROLIDONES

[75] Inventors: Ralph Schmiechen; Reinhard Horowski; Dieter Palenschat; Gert Paschelke; Helmut Wachtel; Wolfgang Kehr, all of Berlin, Fed. Rep. of Germany

[73] Assignee: Schering Aktiengesellschaft, Berlin and Bergkamen, Fed. Rep. of Germany

[21] Appl. No.: 659,082

[22] Filed: Feb. 18, 1976

Related U.S. Application Data

[63] Continuation-in-part of Ser. No. 560,193, Mar. 20, 1975, Pat. No. 4,012,495.

[30] Foreign Application Priority Data

Mar. 20, 1974 [DE] Fed. Rep. of Germany ....... 2413935

[51] Int. Cl.$^2$ ................. C07D 707/26; C07D 405/12; C07D 409/12
[52] U.S. Cl. .............................. 260/326.5 S; 560/42; 260/326.25; 260/326.47; 260/326.55 M; 260/326.45; 260/326.5 FL; 544/141; 544/372; 424/274; 260/340.3; 260/340.5 R; 546/208
[58] Field of Search ............ 260/326.5 FL, 326.5 SM, 260/326.5 S, 326.47, 293.71, 326.25, 247.1 M, 246 B, 293.64, 268 FT, 268 H; 544/141, 372

[56] References Cited

U.S. PATENT DOCUMENTS

| | | | |
|---|---|---|---|
| 3,632,605 | 1/1972 | Debarre | 260/326.47 |
| 3,956,314 | 5/1976 | Strubbe | 260/326.5 FL |

FOREIGN PATENT DOCUMENTS

49/16870 4/1974 Japan .
7503367 8/1975 Netherlands .
1140188 1/1969 United Kingdom .

OTHER PUBLICATIONS

Hackh's Chemical Dictionary, 3rd Edition, p. 687 (1950).

*Primary Examiner*—Mark L. Berch
*Attorney, Agent, or Firm*—Millen & White

[57] ABSTRACT

4-(Polyalkoxyphenyl)-2-pyrrolidones of the formula

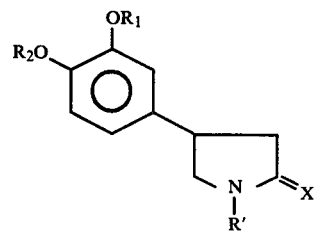

wherein $R_1$ and $R_2$ each are hydrocarbon of up to 18 carbon atoms at least one being other than methyl, a heterocyclic ring, or alkyl of 1–5 carbon atoms substituted by halogen, OH, COOH, alkoxy, alkoxycarbonyl or an amino group; R' is H, alkyl, aryl or acyl; and X is O or S; possess neuropsychotropic activity. The compounds wherein X is O can be produced by saponifying and decarboxylating a corresponding 2-pyrrolidone-3-carboxylic acid alkyl ester or cyclizing a corresponding 3-phenyl-4-amino-butyric acid or alkyl ester thereof. The pyrrolidones can be converted to the corresponding thiopyrrolidones by reaction with phosphorous pentasulfide in the presence of base.

45 Claims, No Drawings

4-(POLYALKOXY PHENYL)-2-PYRROLIDONES

BACKGROUND OF THE INVENTION

This invention relates to novel 4-(polyalkoxyphenyl)-2-pyrrolidones. This is a continuation-in-part of application Ser. No. 560,193, filed Mar. 20, 1975, now U.S. Pat. No. 4,012,495.

British Pat. No. 1,140,188 discloses as intermediates to 2-amino-4-phenyl-1-pyrrolines structurally related 4-phenyl-1-pyrrolidine-2-ones and -2-thiones.

SUMMARY OF THE INVENTION

In a composition aspect, this invention relates to racemic and optically active 4-(polyalkoxyphenyl)-2-pyrrolidones of general Formula I

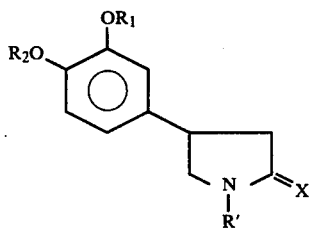

wherein $R_1$ and $R_2$ each are alike or different and are hydrocarbon of up to 18 carbon atoms with at least one being other than methyl, a heterocyclic ring, or alkyl of 1-5 carbon atoms which is substituted by one or more of halogen atoms, hydroxy, carboxy, alkoxy, alkoxycarbonyl or an amino group; amino; R' is a hydrogen atom, alkyl, aryl or acyl; and X is an oxygen atom or a sulfur atom.

In another composition aspect, this invention relates to pharmaceutical compositions comprising one or more compounds of Formula I in admixture with a pharmaceutical carrier.

In process aspects, this invention relates to processes for the production of compounds of Formula I and to methods of using them.

DETAILED DISCUSSION

The compounds of general Formula I possess an asymmetrical carbon atom. Thus, they can be present both as racemates and as optical antipodes thereof.

Examples of hydrocarbon $R_1$ and $R_2$ groups are saturated and unsaturated, straight-chain and branched alkyl of 1-18, preferably 1-5, carbon atoms, cycloalkyl and cycloalkylalkyl, preferably of 3-7 carbon atoms, and aryl and aralkyl, preferably of 6-10 carbon atoms, especially monocyclic.

Examples of alkyl are methyl, ethyl, propyl, isopropyl, butyl, isobutyl, tert.-butyl, pentyl, 2-methylbutyl, 2,2-dimethylpropyl, hexyl, heptyl, octyl, nonyl, 1,2-dimethylheptyl, decyl, undecyl, dodecyl and stearyl, with the proviso that when one of $R_1$ and $R_2$ is methyl, the other is a value other than methyl. Examples of unsaturated alkyl groups are alkenyl and alkinyl, e.g., vinyl, 1-propenyl, 2-propenyl, 2-propinyl and 3-methyl-2-propenyl.

Examples of cycloalkyl and cycloalkylalkyl which preferably contain a total of 3-7 carbon atoms are cyclopropyl, cyclopropylmethyl, cyclopentyl and cyclohexyl.

Examples of aryl and aralkyl are phenyl and benzyl, which are preferred, and tolyl, xylyl, naphthyl, phenethyl and 3-phenylpropyl.

Examples of heterocyclic $R_1$ and $R_2$ groups are those wherein the heterocyclic ring is saturated with 5 or 6 ring members and has a single O, S or N atom as the hetero atom, e.g., 2- and 3-tetrahydrofuryl, 2- and 3-tetrahydropyranyl, 2- and 3-tetrahydrothiophenyl, pyrrolidino, 2- and 3-pyrrolidyl, piperidino, 2-, 3- and 4-piperidyl, and the corresponding N-alkyl-pyrrolidyl and piperidyl wherein alkyl is of 1-4 carbon atoms. Contemplated equivalents are heterocyclic rings having fewer or more, e.g., 4 and 7, ring members, and one or more additional hetero atoms as ring members, e.g., morpholino, piperazino and N-alkylpiperazino.

Examples of substituted alkyl $R_1$ and $R_2$ groups, preferably of 1-5 carbon atoms, are those mono- or polysubstituted, for example, by halogen, especially fluorine, chlorine and bromine. Specific examples of such halogen-substituted alkyl are 2-chloroethyl, 3-chloropropyl, 4-bromobutyl, difluoromethyl, trifluoromethyl, 1,1,2-trifluoro-2-chloroethyl, 3,3,3-trifluoropropyl, 2,2,3,3,3-pentafluoropropyl and 1,1,1,3,3,3-hexafluoro-2-propyl. Examples of other suitable substituents for such alkyl groups are hydroxy groups, e.g., 2-hydroxyethyl or 3-hydroxypropyl; carboxy groups, e.g., carboxymethyl or carboxyethyl; alkoxy groups, wherein each alkoxy group contains 1-5 carbon atoms, e.g., ethoxymethyl, isopropoxymethyl, 2-methoxyethyl, 2-isopropoxyethyl, 2-butyoxyethyl, 2-isobutyoxyethyl, and 3-pentoxypropyl.

Also suitable as preferably terminal-positioned substituents on alkyl groups of 1-5 carbon atoms are alkoxycarbonyl of 1-5 carbon atoms in the alkoxy group. Examples of such alkoxycarbonyl substituted alkyl groups are ethoxycarbonylmethyl and 2-butoxycarbonylethyl.

Alkyl groups of 1-5 carbon atoms can also be substituted, e.g., in the $\beta$, $\gamma$ and preferably terminal position with amino groups wherein the nitrogen atom optionally is mono- or disubstituted by alkyl, preferably of 1-5 carbon atoms, or is part of a 4- to 7-membered ring. Specific examples of amino-substituted alkyl groups are aminomethyl, 2-methylaminoethyl, 2-dimethylaminoethyl, 2-diethylaminoethyl, 3-dimethylaminopropyl, 3-ethylmethylaminopropyl, pyrrolidino, piperidino, morpholino, N-methylpiperazino and hexamethylenimino.

Preferred compounds of general Formula I are those wherein (a) one of $R_1$ and $R_2$ is methyl;

(b) one of $R_1$ and $R_2$ is methyl and the other is hydrocarbon of 2-18 carbon atoms, e.g., alkyl or alkenyl of 2-18 carbon atoms;

(c) one of $R_1$ and $R_2$ is methyl and the other is cycloalkyl or cycloalkylalkyl of 3-7 carbon atoms;

(d) one of $R_1$ and $R_2$ is methyl and the other is hydrocarbon aryl or aralkyl of 6-10 carbon atoms;

(e) one of $R_1$ and $R_2$ is methyl and the other is a heterocyclic ring, preferably tetrahydrothienyl or tetrahydrofuryl;

(f) one of $R_1$ and $R_2$ is methyl and the other is substituted alkyl, preferably mono-, di- or trihaloalkyl;

(g) X is O, especially those of (a)-(f);

(h) X is S, especially those of (a)-(f); and (i) R' is H, especially those of (a)-(h).

Examples of R' groups, in addition to hydrogen, are lower alkyl of 1 to 4 carbon atoms, e.g., methyl and ethyl, aryl, e.g., phenyl or other hydrocarbon aryl as illustrated above for $R_1$ and $R_2$, lower acyl, preferably alkanoyl of 1–6 carbon atoms, e.g., acetyl, propionyl, butyryl and pivaloyl. Other examples of aryl are those as illustrated above for $R_1$ and $R_2$. When R' is acyl, the exact nature of the acylating group is not critical, since activity resides in the N-unsubstituted moiety. Thus, equivalents of the preferred lower-alkanoyl R' groups are those of the formula RCO— wherein R is a hydrocarbon or substituted alkyl group as illustrated above for $R_1$ and $R_2$.

The racemic and optically active compounds of general Formula I are valuable neuropsychotropic medicinal agents. The novel compounds exhibit central-depressive, apomorphine antagonistic and antinociceptive effects and this exhibit a response spectrum similar to chlorpromazine (literature: Modern Problems of Pharmacopsychiatry, vol. 5, pp. 33–44: Janssen P. A. Y., "Chemical and Pharmacological Classification of Neuroleptics," edited by Bobon D. P. et al., S. Karger publishers, Basel-Munich-Paris-New York [1970]). On the other hand, the compounds of the present invention differ from chlorpromazine by a less pronounced reflex impairment, less pronounced sedative and narcotic properties, and by a different influence on the biogenous amines. Thus, for example, 4-(3,4-dimethoxyphenyl)-2-pyrrolidone has a barbital-sleep time prolonging effect which is about 20 times weaker than that of chlorpromazine.

The novel compounds are characterized by a rapid onset of effectiveness and a low order of acute toxicity.

The advantageous properties of the novel compounds is surprising because, as demonstrated in tests conducted in our laboratories, the corresponding p- and m-monosubstituted phenyl-2-pyrrolidones have, respectively, a different spectrum of activity or an only minor activity.

For example, 4-(4-chlorophenyl)-2-pyrrolidone, described in Japanese Pat. No. 70 16 692, has an anticonvulsive effect. The unsubstituted phenyl-2-pyrrolidones have only very weak activity.

The compounds of this invention can be used in the form of pharmaceutical compositions for the treatment of various neurological and psychic disorders, especially as neuroleptics having diminished extrapyramidal symptomatology, for example, schizophrenia and related psychotic states characterized by anxiety, hostility, agression, withdrawal, halluzination, thought-disturbances, delusion and agitation. The compounds of this invention are thus useful for the treatment of such disorders responding to chlorpromazine therapy.

The pharmaceutical compositions of this invention can be formulated using the vehicles customary for enteral or parenteral administration, such as, for example, water, alcohol, gelatin, gum arabic, lactose, amylose, magnesium stearate, talc, vegetable oils, polyalkylene glycol, etc. The preparations can be formulated in solid form, e.g., as tablets, capsules, dragees and suppositories, or in the liquid form, e.g., as solutions, suspensions and emulsions.

Although a single racemate or optical antipode of Formula I are generally employed in such compositions, mixtures thereof can also be employed, if desired.

For oral administration, the amount of active agent per oral dosage unit usually is 1–20 mg., preferably 5–10 mg. The daily dosage is usually 1–50 mg., preferably 10–30 mg. p.o. For parenteral application, the amount of active agent per dosage unit is usually 0.05–10 mg., preferably 0.1–5 mg. The daily dosage is usually 0.1–20 mg., preferably 0.2–5 mg. i.v. or i.m.

The novel 4-(polyalkoxyphenyl)-2-pyrrolidones of general Formula I can be produced by means of conventional reactions wherein (a) 4-(substituted phenyl)-2-pyrrolidone-3-carboxylic acid alkyl esters of general Formula II

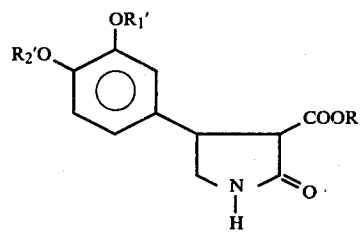

wherein $R_1'$ and $R_2'$ are $R_1$ and $R_2$, respectively, or hydrogen and R is acyl, preferably lower acyl, are saponified and decarboxylated; or (b) 3-(substituted phenyl)-4-aminobutyric acid alkyl esters of general Formula III

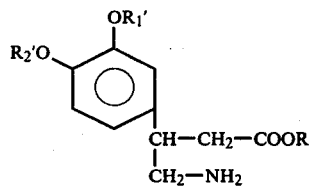

wherein $R_1'$, $R_2'$ and R have the values given above or an acid addition salt thereof, are cyclized with splitting off of an ROH alcohol; or (c) 3-(substituted phenyl)-4-aminobutyric acid of the general Formula IV

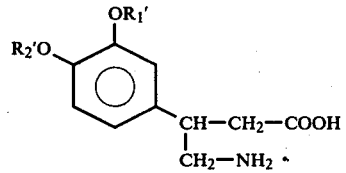

wherein $R_1'$, and $R_2'$ have the values given above or an acid addition salt thereof, is cyclized with splitting off of water; and optionally, in the compounds obtained according to (a), (b) or (c) a a free hydroxy group ($OR_1'$ or $OR_2'$) is alkylated or arylated, and/or a free imino group (NH) is alkylated, arylated or acylated, and/or the carbonyl oxygen is exchanged with sulfur; and/or a racemate is subjected to a racemate splitting step and one or both optically active antipodes thereof are isolated.

Conventional methods are employed for the preparation of the compounds according to general Formula I.

The saponification according to method (a) is accomplished with aqueous alkali, suitably in a water-miscible solvent, e.g., in an alcohol, such as ethanol, in tetrahydrofuran, or in dioxane at temperatures of between approximately 60° C. and 150° C., preferably at the boiling temperature. The decarboxylation according to (a) takes place by heating the carboxylic acid to about 160°–280° C. Preferably, the compound is heated under vacuum. The $CO_2$ can also be split off optionally in the presence of a high-boiling inert solvent, e.g., diphenyl ether or quinoline.

The cyclization according to method (b) is effected, while splitting off alcohol, in an organic solvent such as, for example, dimethylformamide, dimethylacetamide, tetrahydrofuran, dioxane, benzene, toluene, xylene, etc., while heating the reaction mixture to about 50°–150° C. When starting with a salt, e.g., the hydrochloride, of the amino acid ester of general Formula III, the mixture is heated in the presence of a tertiary base. Suitable tertiary bases are trialkylamines, for example, triethylamine and tributylamine, as well as, for example, N-methylmorpholine, diethylcyclohexylamine, pyridine, etc.

According to method (c), the cyclization is conducted while splitting off water at temperatures of between about 160° and 280° C. It is advantageous to work under a vacuum so that the split-off water can be more easily removed and the access of atmospheric oxygen is prevented. When starting with the corresponding acid addition salts, the reaction is carried out, as under (b), by heating in the presence of a tertiary base.

The compounds obtained according to (a), (b), or (c) wherein $R_1'$ or $R_2'$ is a hydrogen atom must subsequently be converted into the final products of general Formula I by O-alkylation. The alkylation is preferably conducted in a conventional manner with the corresponding $R_1$- and/or $R_2$-halogenide or -tosylate. Suitable halogenides are the chlorides, bromides, and iodides. For purposes of the alkylation, the hydroxy compound is, for example, dissolved in a polar solvent and heated to temperatures of between 30° and 150° C. in the presence of a base together with the alkylating agent. Examples of bases are sodium hydride, potassium carbonate, alkali alcoholates, such as sodium ethylate, potassium butylate, and potassium tert.-butylate, of polar solvents, dimethylformamide, dimethylacetamide, tetrahydrofuran, dioxane, ketones, such as acetone and methyl isobutyl ketone, as well as alcohols, such as ethanol, butanol, and tert.-butanol.

The alkylation, arylation, or acylation of the imino group likewise take place according to conventional methods. Thus, the imino compound ($R_1$=H) is dissolved in a polar solvent and heated to about 40°–150° C. in the presence of a salt-forming agent with an alkyl, aryl, or acyl halogenide. Suitable polar solvents are dimethylformamide, dimethylacetamide, tetrahydrofuran, dioxane, ketones such as acetone and methyl isobutyl ketone, as well as alcohols, such as ethanol and butanol. Suitable salt-forming agents are, for example, sodium hydride, potassium carbonate, alkali alcoholates, such as sodium ethylate, potassium tert.-butylate, etc. The reaction with a haloaryl, e.g., iodobenzene, can also be effected without a solvent, preferably in the presence of pulverized copper.

The exchange of the carbonyl oxygen against sulfur is conducted in the same way as described in the literature for such compounds. (Compare, in this connection, J. W. Scheeren, P. H. J. Ohms, R. J. F. Nivard, Synthesis 1973, 149–151.) Suitable for this purpose is, for example, a polysulfide, such as phosphorus pentasulfide, in a solvent or solvent mixture in the presence of a base. The reaction can also be effected in a suspension. Suitable solvents or suspension agents are, for instance, acetonitrile, tetrahydrofuran, diethyl ether, glycol dimethyl ether. Advantageous bases are sodium bicarbonate, potassium carbonate, etc. The reaction is terminated, at 30°–120° C., after 3–24 hours.

The starting compounds of Formulae II, III, and IV can likewise be prepared according to known methods, for example in the following ways:

Starting with the benzaldehyde substituted by $R_1'$, and $R_2'$, the corresponding benzal-malonic acid dialkyl ester is produced with the dialkyl ester of malonic acid. The substituted benzal-malonic acid dialkyl ester can be converted with nitromethane in the presence of tetramethylguanidine, by way of the 1-(substituted phenyl)-2-nitroethylmalonic acid dialkyl ester and subsequent pressurized hydrogenation with the use of Raney nickel, into 4-(substituted phenyl)-2-pyrrolidone-3-carboxylic acid alkyl esters of the general Formula II.

To produce 3-(substituted phenyl)-4-aminobutyric acid alkyl esters of general Formula III, HCN is added to the double bond of the benzal-malonic acid diester with potassium cyanide in aqueous alcohol under heating to 60° C., with the simultaneous splitting off of a carbalkoxy group; and the cyano compound is hydrogenated under pressure in the presence of platinum dioxide. If the addition of HCN is conducted under boiling heat, the corresponding butyric acid of general Formula IV is obtained.

The reactions of the substituted benzaldehyde to obtain the compounds of Formulae II, III, and IV will be explained once more with reference to the following reaction scheme:

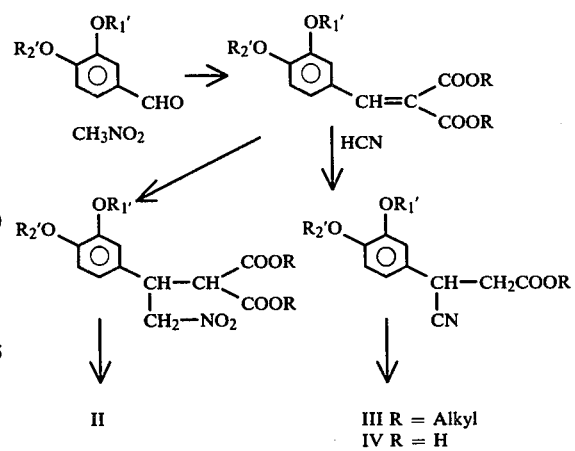

III R = Alkyl
IV R = H

The processes will be described in greater detail below.

The term "worked up as usual" means extraction with the indicated solvent, washing of the organic phase with saturated NaCl solution, drying over anhydrous calcium sulfate, and evaporation under vacuum at a bath temperature of 40°–45° C. Specific mention is made of any additional treatment of the organic base, such as washing with acid or an alkali.

The indicated yields are not optimum values. No attempts at optimization have been made.

The temperatures are indicated in degrees Celsius (°C.).

The compounds set forth as starting materials were tested for sufficient purity by thin-layer chromatography in at least two systems and with the aid of IR spectra. All other substances are analytically pure (C, H, N determinations; IR, UV, and NMR spectra; thin-layer chromatography; partially titrations and gas chromatography).

Adjacent the melting point, determined on the Kofler heating bench, the solvents used for the recrystallization are indicated in parentheses.

The following abbreviations are employed for solvents:
DMF: dimethylformamide
EE: ethyl acetate
DIP: diisopropyl ether
W: water
AcOH: glacial acetic acid
Bz: benzene The compounds of general Formula II can be prepared, for example, as follows:

(A) Benzal-Malonic Acid Diethyl Ester

One mole of a correspondingly substituted benzaldehyde is heated on a water trap with 160 g. (1 mole) of diethyl malonate, 30 ml. of glacial acetic acid, and 3 ml. of piperidine in 1 liter of benzene until 1 mole of water has been split off. The benzenic solution is worked up as usual.

3-Isobutoxy-4-methoxybenzaldehyde, not heretofore described in the literature, is prepared as follows:

108 g. of 3-hydroxy-4-methoxybenzaldehyde (710 millimoles) is heated for 26 hours to the boiling point with 40.5 g. of potassium hydroxide (723 mmol) and 120 g. of isobutyl bromide (875 mmol) in 250 ml. of ethanol under agitation. After the alcohol has been distilled off under vacuum, the residue is worked up as usual with ethyl acetate, but washed additionally with 2 N sodium hydroxide solution. By acidification, 35 g. of starting material is recovered from the alkaline extract. The yield of 3-isobutoxy-4-methoxybenzaldehyde is 80 g.; m.p. 70° (heptane).

In the following table, the yields as well as the boiling and melting points of several compounds have been compiled:

(A)

$$\text{R}_2'\text{O}-\text{C}_6\text{H}_3(\text{OR}_1')-\text{CH}=\text{C}(\text{COOC}_2\text{H}_5)_2$$

| | $R_1'$ | $R_2'$ | Yield (% of Theory) | Boiling point Melting point (Recrystallization Agent) |
|---|---|---|---|---|
| a | —CH₃ | —CH₃ | 70 | b.p.₀.₆ 185°–189° |
| b | —CH₂— | | 53 | b.p.₀.₄ 172° |
| c | —CH₂CH₂— | | 88 | b.p.₁ 227°–289° |
| d | —CH₂CH(CH₃)₂— | —CH₃ | 95 | b.p.₀.₁ 190°–192° |
| e | —H | —CH₃ | 78 | b.p.₁ 213°–215° m.p. 86° (DIP) |
| f | —CH₃ | —H | 77 | m.p. 121° (DIP) |

(B) 1-(Substituted Phenyl)-2-nitroethylmalonic Acid Diethyl Ester 500 millimoles of the corresponding benzal-malonic acid diethyl ester (see [A]) is dissolved in 250 ml. of nitromethane and combined with 12.7 ml. of tetramethylguanidine under agitation at 0°. After the exothermic reaction has faded, the mixture is further stirred at room temperature for 18 hours. Then, the mixture is worked up as usual with ethyl acetate, but additionally washed with 2 N hydrochloric acid. The acetoxymethoxybenzal-malonic esters required for Examples B(b) and B(c) are produced as follows:

150 g. of (3-hydroxy-4-methoxybenzal)-malonic acid diethyl ester (510 mmol) (see A[e]) is dissolved in 450 ml. of pyridine and, under ice cooling, 57 ml. of acetic anhydride (604 mmol) is added thereto dropwise. After allowing the reaction mixture to stand for 18 hours at room temperature, the pyridine is withdrawn under vacuum. The mixture is worked up as usual with ethyl acetate, yielding 163 g. of (3-acetoxy-4-methoxybenzal)-malonic acid diethyl ester (95% of theory); m.p. 75°–77° (diisopropyl ether).

Analogously, the (4-hydroxy-3-methoxybenzal)-malonate (see A[f]) is acetylated to the corresponding 4-acetoxy-3-methoxy compound. Yield: 95%. M.p. 51° (diisopropyl ether—petroleum ether).

(B)

$$\text{R}_2'\text{O}-\text{C}_6\text{H}_3(\text{OR}_1')-\text{CH}(\text{CH}_2\text{NO}_2)-\text{CH}(\text{COOC}_2\text{H}_5)_2$$

| | $R_1'$ | $R_2'$ | Yield (% of Theory) | Melting point (Recrystallizing Agent) |
|---|---|---|---|---|
| a | —CH₃ | —CH₃ | 59 | 75° (methylene chloride - DIP) |
| b | —COCH₃ | —CH₃ | 95 | crude product (TLC, IR) |
| c | —CH₃ | —COCH₃ | 95 | crude product (TLC, IR) |

(C) 4-(Substituted Phenyl)-2-pyrrolidone-3-carboxylic Acid Ethyl Ester (II)

300 millimoles of the corresponding 1-phenyl-2-nitroethylmalonic acid diethyl ester is dissolved in 700 ml. of methanol and hydrogenated with about 10 g. of Raney nickel at 60° and under a pressure of 95 atmospheres until 3 moles of hydrogen have been absorbed. Thereafter, the product is filtered off from the catalyst, concentrated under vacuum, and the oily residue is recrystallized.

(C)

$$\text{R}_2'\text{O}-\text{C}_6\text{H}_3(\text{OR}_1')-\text{C}_4\text{H}_5\text{NO}(\text{COOC}_2\text{H}_5)$$

| | $R_1'$ | $R_2'$ | Yield (% of Theory) | Melting point (Recrystallizing Agent) |
|---|---|---|---|---|
| a | —CH₃ | —CH₃ | 84 | 106° (EE) |
| b | —H | —CH₃ | 70 | 125° (EE-DIP) (splitting off the acetyl group during hydrogenation, and work-up step) |
| c | —CH₃ | —COCH₃ | 62 | 172° (EE) |

The compounds of general Formula III can be produced, for example, as follows:

(D) 3-(Substituted Phenyl)-3-cyanopropionic Acid Ethyl Ester 100 millimoles of a corresponding benzal-malonic ester (see [A]) is combined, in 180 ml. of ethanol, with a solution of 6.5 g. of potassium cyanide (100 mmol) in 25 ml. of water and heated for 7 hours to 60°. After allowing the mixture to stand for 18 hours at room temperature, the solvents are removed under vacuum, and the residue is worked up as usual with ethyl acetate, including an extraction with 1 N sodium hydroxide solution. If desired, the corresponding 3-phenyl-3-cyanopropionic acid ethyl esters can be obtained by acidification from the sodium hydroxide solution extract.

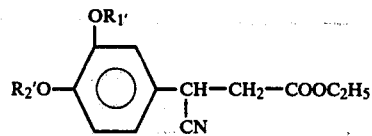
(D)

| $R_1'$ | $R_2'$ | Yield (% of Theory) | Boiling point Melting point (Recrystallizing Agent) |
|---|---|---|---|
| a | —CH$_3$ | —CH$_3$ | 85 | b.p.$_{0.1}$ 177°–182° |
| b | —CH$_2$— | | 82 | crude product (TLC, IR) |
| c | —CH$_2$CH$_2$— | | 84 | crude product (TLC, IR) |
| d | —CH$_2$CH(CH$_3$)$_2$ —CH$_3$ | | 83 | crude product (TLC, IR) |
| e | —CH$_3$ | —H | 91 | crude product (TLC, IR) |

(E) 3-(Substituted Phenyl)-4-aminobutyric Acid Ethyl Ester Hydrochloride (III)

50 millimoles of a 3-phenyl-3-cyanopropionic acid ethyl ester is hydrogenated in 60 ml. of glacial acetic acid over 1 g. of platinum oxide at room temperature and 100 atmospheres until 2 moles of hydrogen have been absorbed. The reaction product is filtered off from the catalyst under vacuum and, after adding 25 ml. of 2 N methanolic hydrochloric acid, evaporated under vacuum to a small volume.

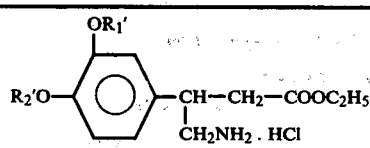
(E)

| | $R_1'$ | $R_2'$ | Yield (% of Theory) | Melting point (Recrystallizing Agent) |
|---|---|---|---|---|
| a | —CH$_3$ | —CH$_3$ | 90 | m.p. 185° (AcOH) |
| b | —CH$_2$— | | 79 | crude product (TLC, IR) |
| c | —CH$_2$CH$_2$— | | 100 | crude product (TLC, IR) |
| d | —CH$_2$CH(CH$_3$)$_2$ —CH$_3$ | | 63 | m.p. 124° (EE) |

The compounds of general Formula IV can be prepared as follows:

(F) 3-(Substituted Phenyl)-3-cyanopropionic Acid

By reacting a correspondingly substituted benzalmalonic ester (see under [A]) with potassium cyanide in the same quantitative ratios and with the same reaction times as described under (D), but under boiling heat, the 3-(substituted phenyl)-3-cyanopropionic acids are obtained. These acids are isolated after evaporation of the solvents, taking up the residue in water, washing with ethyl acetate, and acidification of the aqueous phase; the products are purified by crystallization.

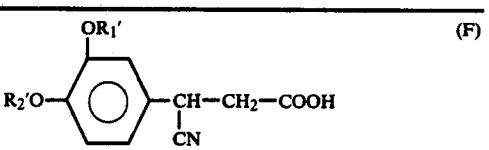
(F)

| | $R_1'$ | $R_2'$ | Yield (% of Theory) | Melting point (Recrystallizing Agent) |
|---|---|---|---|---|
| a | —CH$_3$ | —CH$_3$ | 54 | m.p. 133°–135° (ethanol) |
| b | —CH$_2$— | | 63 | crude product (TLC, IR) |
| c | —CH$_2$CH$_2$— | | 76 | crude product (TLC, IR) |

(G) 3-(Substituted Phenyl)-4-aminobutyric Acid Hydrochloride (IV)

100 millimoles of 3-(substituted phenyl)-3-cyanopropionic acid (see [F]) is hydrogenated in 200 ml. of glacial acetic acid with the addition of 9.5 ml. of concentrated hydrochloric acid over 3 g. of platinum dioxide at room temperature and 100 atmospheres until 2 moles of hydrogen have been absorbed. The product is filtered off from the catalyst and concentrated under vacuum. The 3-(substituted phenyl)-4-aminobutyric acid hydrochlorides are obtained by crystallization of the mostly oily residue.

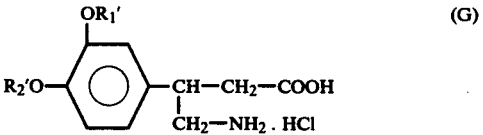
(G)

| | $R_1'$ | $R_2'$ | Yield (% of Theory) | Melting point (Recrystallizing Agent) |
|---|---|---|---|---|
| a | —CH$_3$ | —CH$_3$ | 50 | m.p. 220° (decomp.) (AcOH) |
| b | —CH$_2$— | | 43 | m.p. 210° (1N HCl) |
| c | —CH$_2$CH$_2$— | | 52 | m.p. 207° (ethanol-DIP) |

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

4-(Substituted Phenyl)-2-pyrrolidones

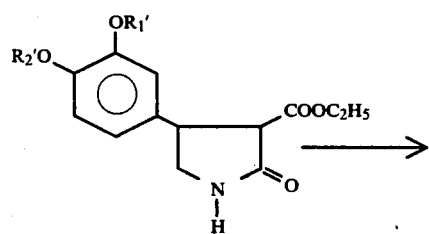

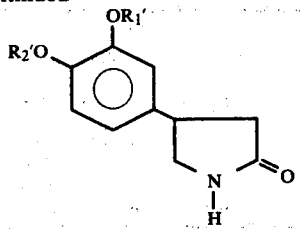

50 millimoles of a 4-(substituted phenyl)-2-pyrrolidone-3-carboxylic acid ethyl ester (according to [C]) is heated to the boiling point for 1 hour with 200 ml. of ethanol and 60 ml. of 1 N sodium hydroxide solution. After the solvents have been distilled off under vacuum, the residue is taken up in ethyl acetate and extracted with water, optionally while adding some sodium hydroxide solution. After saturation with NaCl, 4-(substituted phenyl)-2-pyrrolidone-3-carboxylic acid is precipitated from the aqueous phase with 5 N hydrochloric acid. After allowing the reaction mixture to stand for a certain time under cold conditions, the reaction mixture is vacuum-filtered and washed with a small amount of ice water. Decarboxylation of the pyrrolidone-carboxylic acid takes place by heating to 200° under vacuum until the evolution of $CO_2$ has ceased. The residue is recrystallized, optionally while adding carbon.

| | $R_1'$ | $R_2'$ | Yield (% of Theory) | Boiling point Melting point (Recrystalliz- ing Agent) |
|---|---|---|---|---|
| a | —CH₃ | —CH₃ | 81 | 120° (W) |
| b | —H | —CH₃ | 45 | 144° (isopropanol) |
| c | —CH₃ | —H | 40 | b.p.₀.₆ 230° (*) |

(*)Chromatography on silica gel (Bz. AcOH-H₂O, 10:10:1) under simultaneous saponification of the 4-acetoxy group.
1(a) 4-(3,4-dimethoxyphenyl)-2-pyrrolidone
1(b) 4-(3-hydroxy-4-methoxyphenyl)-2-pyrrolidone
1(c) 4-(4-hydroxy-3-methoxyphenyl)-2-pyrrolidone

EXAMPLE 2

4-(Substituted Phenyl)-2-pyrrolidones

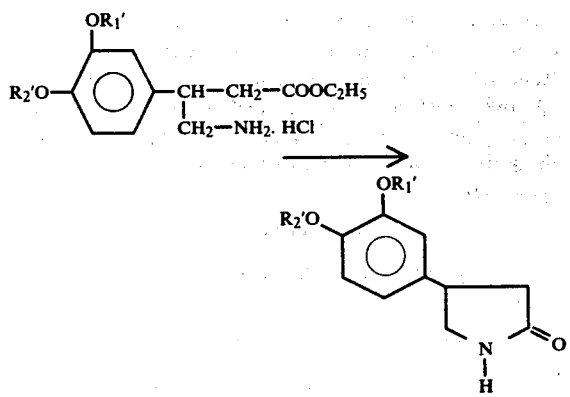

Method I 10 millimoles of a 3-(substituted phenyl)-4-aminobutyric acid ethyl ester hydrochloride is dissolved in 15 ml. of dimethylformamide, combined with 1.4 ml. of triethylamine (10 mmol), and heated for 6 hours to 70°. After evaporation under vacuum, the mixture is worked up as usual with ethyl acetate.

Method II

Under agitation, 10 mmol of a 3-(substituted phenyl)-4-aminobutyric acid ethyl ester hydrochloride and 1.4 ml. of triethylamine (10 mmol) are heated in 50 ml. of benzene to the boiling point until the ninhydrin reaction is negative; the mixture is then worked up as usual.

| Method | $R_1'$ | $R_2'$ | Yield (% of Theory) | Boiling point Melting point (Recrystalliz- ing Agent |
|---|---|---|---|---|
| a | I | —CH₃ | —CH₃ | 63 | m.p. 120° (W) |
| b | II | —CH₂— | | 49 | m.p. 157° (EE) |
| c | II | —CH₂CH₂— | | 54 | m.p. 104° (EE) |
| d | II | —CH₂CH(CH₃)₂ CH₃ | | 50 | m.p. 150° (EE) |
| e | I | —CH₃ | —H | 10 | b.p.₀.₆ 230° chromatography on SiO₂ (Bz - AcOH-H₂O, 10:10:1) |

2(a) 4-(3,4-dimethoxyphenyl)-2-pyrrolidone
2(b) 4-(3,4-methylenedioxyphenyl)-2-pyrrolidone
2(c) 4-(3,4-ethylenedioxyphenyl)-2-pyrrolidone
2(d) 4-(3-isobutoxy-4-methoxyphenyl)-2-pyrrolidone
2(e) 4-(4-hydroxy-3-methoxyphenyl)-2-pyrrolidone

EXAMPLE 3

4-(3,4-Dimethoxyphenyl)-2-pyrrolidone

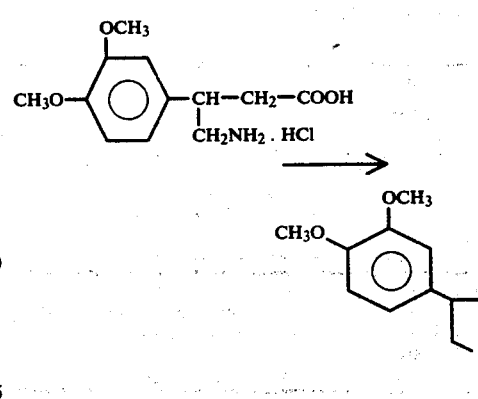

2.76 g. of 4-amino-3-(3,4-dimethoxyphenyl)-butyric acid hydrochloride is combined with 1.4 ml. of triethylamine (10 mmol) in 1-2 ml. of ethanol and then heated under vacuum (0.4-0.6 torr [mm. Hg]) to 200°-210° until no free amino acid can be detected any longer by a spot analysis with ninhydrin. The usual working up procedure with ethyl acetate yields, from the residue, 1.26 g. of 4-(3,4-dimethoxyphenyl)-2-pyrrolidone (57% of theory); m.p. 120° (water).

EXAMPLE 4

4-(Alkoxymethoxyphenyl)-2-pyrrolidones

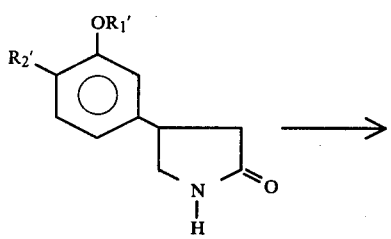

→

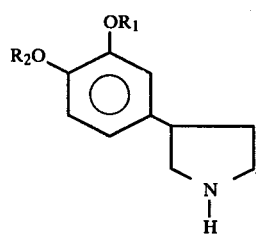

Method A

10 millimoles of a 4-(hydroxyalkoxyphenyl)-2-pyrrolidone is dissolved in 5 ml. of dimethylformamide, combined under ice cooling with 500 mg. of a 50% sodium hydride—paraffin oil suspension (10.5 mmol), and heated gradually to 60° under agitation. After the evolution of hydrogen has ceased, 11 mmol of the corresponding R-halogenide and 100 mg. of sodium iodide in 3 ml. of dimethylformamide are added thereto at 0°, and the mixture is heated for 3 hours to 100° under agitation. Then, the solvent is distilled off under vacuum and the residue worked up as usual with ethyl acetate, including an extraction with 2 N sodium hydroxide solution.

Method B

10 millimoles of a 4-(hydroxyalkoxyphenyl)-2-pyrrolidone, 11 mmol of the corresponding halogenide, and 1.45 g. of potassium carbonate (10.5 mmol) are heated in 30 ml. of acetone for 38 hours under agitation to the boiling point. The residue remaining after the inorganic salts have been vacuum-filtered and the residue evaporated under vacuum is worked up as indicated in method A.

Method C

10 millimoles of a 4-(hydroxyalkoxyphenyl)-2-pyrrolidone is dissolved in 22 ml. of 0.5 N sodium butylate solution in butanol and heated to the boiling point with 11 mmol of the corresponding halogenide for 10 hours under agitation. The reaction mixture is worked up as described under method A.

| $R_2=CH_3$ | $R_1$ | Method | Yield (% of Theory) | Melting Point (Recyrstallizing Agent) |
|---|---|---|---|---|
| a | $-C_2H_5$ | C | 62 | 123° (EE) |
| b | $-C_3H_7$ | B | 42 | 124° (EE-DIP) |
| c | $-C_4H_9$ | C | 47 | 125° (DIP) |
| d | $-C_6H_{13}$ | A | 48 | 119° (EE-DIP) |
| e | $-CH(CH_3)_2$ (−CH with CH₃, CH₃) | A | 44 | 123° (EE-DIP) |
| f | −CH(CH₃)(C₂H₅) | B | 41 | 105° (EE-DIP) |
| g | −CH₂−CH(CH₃)₂ | B | 40 | 150° (EE) |
| h | $-CH_2-CH=CH_2$ | B | 46 | 104° (EE-DIP) |
| i | −CH₂−CH=C(CH₃)₂ | B | 38 | 123° (EE-DIP) |
| k | $-CH_2OCH_3$ | A | 38 | 94° (triturate with DIP) |
| l | $-CH_2-CON(C_2H_5)_2$ | A | 56 | 117° (EE-petroleum ether) |
| m | $-CH_2CH_2OH$ | A | 34 | 108° (EE) |
| n | $-CH_2CF_3$ | B | 36 | 110° (EE) |
| o | −CH₂−C₆H₅ 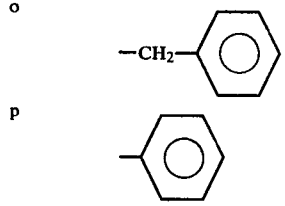 | A | 57 | 132° (EE) |
| p |  | $K_2CO_3$, DMF 30' | 71 | 132° (EE) |

-continued
| R₂=CH₃ | R₁ | Method | Yield (% of Theory) | Melting Point (Recyrstalliz- ing Agent) |
|---|---|---|---|---|
| | | | | 130° |
| a' | —C₁₀H₂₁ | A | 49 | 117° (EE) |
| b' | —C₁₈H₃₇ | A | 40 | 119° (EE) |
| c' | —CH₂—CH(CH₃)(C₂H₅) | A | 50 | 140° (EE) |
| d' | —CH₂—C(CH₃)₃ | A | 21 | 166° (EE-DIP) |
| e' | —CH₂—CH₂—CH(CH₃)₂ | A | 61 | 139° (EE) |
| f' | —CH₂—C≡CH | A* | 60 | 116° (EE-DIP) |
| g' | —CH₂—C≡N | A | 48 | 144° (EE-DIP) |
| h' | 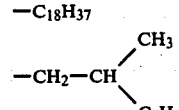 | A | 20 | 140° (EE-DIP) |
| i' | 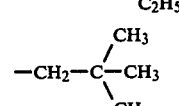 | A* | 30 | 132° (EE) |
| k' | 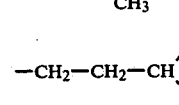 | A | 20 | 128° (EE-DIP) |
| l' | 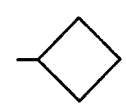 | A** | 22 | 128° (EE-DIP) |
| m' | 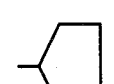 | A** | 19 | 120° (EE-DIP) |
| n' | 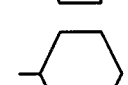 | A | 12 | 128°* |
| o' | 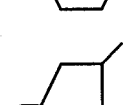 | A | 20 | 107°* |
| p' | —CH₂—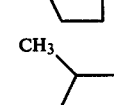 | A | 50 | 123° (EE) |
| q' | —CH₂—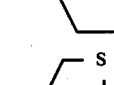 | A** | 36 | 132° (EE-Hexane) |
| | 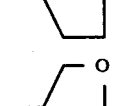 | A | 32 | 173°–176° (Ethanol) |

| $R_2=CH_3$ $R_1$ | Method | Yield (% of Theory) | Melting Point (Recyrstallizing Agent) |
|---|---|---|---|
| s' —CH₂—C(=CH₂)CH₃ | B | 63 | 130° (EE-DIP) |

*Using hexamethylphosphoric triamide instead of DMF
**The tosylate was used instead of the R-halogenide
***Chromatography on SiO₂, CH₂Cl₂-acetone (1:1)

| $R_1=CH_3$ | $R_2$ | Method | Yield (% of Theory) | Melt. Pt. (Recryst. Agent) |
|---|---|---|---|---|
| q | —C₂H₅ | C | 47 | 168° (EE) |
| r | —C₄H₉ | C | 62 | 118° (DIP) |
| s | —CH₂—CON(C₂H₅)₂ | A | 53 | 95° (EE) |
| t' | —CH₂—C≡CH | A(*) | 61 | 126° (EE) |
| u' | (cyclopentyl) | A(*) | 62 | 104° (EE) |

| $R_1=R_2$ | $R_2$ | Method | Yield (% of Theory) | Melt. Pt. (Recryst. Agent) |
|---|---|---|---|---|
| v' | —C₂H₅ | A(+) | 83 | 146–148° (EE- DIP) |
| w' | —CH₂—CH(CH₃)CH₃ | A(+) | 42 | 88° (hexane) |

(*)Using haxamethylphosphoric triamide instead of DMF.
(+)Method A, but using 4-(3,4-dihydroxyphenol)-2-pyrrolidone as the starting material.

4 a 4-(3-ethoxy-4-methoxyphenyl)-2-pyrrolidone
  b 4-(3-propoxy-4-methoxyphenyl)-2-pyrrolidone
  c 4-(3-butoxy-4-methoxyphenyl)-2-pyrrolidone
  d 4-(3-hexyloxy-4-methoxyphenyl)-2-pyrrolidone
  e 4-(3-isopropoxy-4-methoxyphenyl)-2-pyrrolidone
  f 4-(3-[1-methylpropoxy]-4-methoxyphenyl)-2-pyrrolidone
  g 4-(3-isobutoxy-4-methoxyphenyl)-2-pyrrolidone
  h 4-(3-allyloxy-4-methoxyphenyl)-2-pyrrolidone
  i 4-(3-[3-methyl-2-butenyloxy]-4-methoxyphenyl)-2-pyrrolidone
  k 4-(3-methoxymethoxy-4-methoxyphenyl)-2-pyrrolidone
  l 4-(3-diethylaminocarbonylmethoxy-4-methoxyphenyl)-2-pyrrolidone
  m 4-(3-[2-hydroxyethoxy]-4-methoxyphenyl)-2-pyrrolidone
  n 4-(3-[2,2,2-trifluoroethoxy]-4-methoxyphenyl)-2-pyrrolidone
  o 4-(3-benzyloxy-4-methoxyphenyl)-2-pyrrolidone
  p 4-(3-phenoxy-4-methoxyphenyl)-2-pyrrolidone
  q 4-(3-methoxy-4-ethoxyphenyl)-2-pyrrolidone
  r 4-(3-methoxy-4-butoxyphenyl)-2-pyrrolidone
  s 4-(3-methoxy-4-diethylaminocarbonylmethoxyphenyl)-2-pyrrolidone
4 a' 4-(3-decyloxy-4-methoxyphenyl)-2-pyrrolidone
  b' 4-(3-octadecyloxy-4-methoxyphenyl)-2-pyrrolidone
  c' 4-(3-[2-methylbutyl]-oxy-4-methoxyphenyl)-2-pyrrolidone
  d' 4-(3-neopentyloxy-4-methoxyphenyl)-2-pyrrolidone
  e' 4-(3-isopentyloxy-4-methoxyphenyl)-2-pyrrolidone
  f' 4-(3-[2-propinyl]-oxy-4-methoxyphenyl)-2-pyrrolidone
  g' 4-(3-cyanomethyloxy-4-methoxyphenyl)-2-pyrrolidone
  h' 4-(3-cyclobutoxy-4-methoxyphenyl)-2-pyrrolidone
  i' 4-(3-cyclopentyloxy-4-methoxyphenyl)-2-pyrrolidone
  k' 4-(3-cyclohexyloxy-4-methoxyphenyl)-2-pyrrolidone
  l' 4-(3-[3-methylcyclopentyl]-oxy-4-methoxyphenyl)-2-pyrrolidone
  m' 4-(3-[2-methylcyclopentyl]-oxy-4-methoxyphenyl)-2-pyrrolidone
  n' 4-(3-[3-tetrahydrothienyl]-4-methoxyphenyl)-2-pyrrolidone
  o' 4-(3-[3-tetrahydrofuryl]-oxy-4-methoxyphenyl)-2-pyrrolidone
  p' 4-(3-cyclopropylmethyloxy-4-methoxyphenyl)-2-pyrrolidone
  q' 4-(3-cyclopentylmethyloxy-4-methoxyphenyl)-2-pyrrolidone
  r' 4-(3-[2-oxacyclopentyloxy]-4-methoxyphenyl)-2-pyrrolidone
  s' 4-(3-methallyloxy-4-methoxyphenyl)-2-pyrrolidone
  t' 4-(4-propinyloxy-3-methoxyphenyl)-2-pyrrolidone
  u' 4-(4-cyclopentyloxy-3-methoxyphenyl)-2-pyrrolidone
  v' 4-(3,4-diethoxyphenyl)-2-pyrrolidone
  w' 4-(3,4-diisobutoxyphenyl)-2-pyrrolidone.

The starting material for producing the compounds 4 v' and 4 w' (4-[3,4-dihydroxyphenyl]-2-pyrrolidone) is prepared from the dimethyl ether 1 a as follows:

4.75 g. of 4-(3,4-dimethoxyphenyl)-2-pyrrolidone (20 mmol) is dissolved in 130 ml. of methylene chloride and at −80° combined dropwise under the exclusion of moisture and under agitation with 11.0 g. of boron tribromide (44 mmol), dissolved in 40 ml. of methylene chloride. The mixture is allowed to warm up to room temperature overnight, poured into water, and the crystalline precipitate is vacuum-filtered. The aqueous phase is extracted with ethyl acetate after saturation with NaCl. The ethyl acetate extract is concentrated by evaporation, and the residue is recrystallized from water together with the crystalline precipitate, thus obtaining 3.35 g. of 4-(3,4-dihydroxyphenyl)-2-pyrrolidone, m.p. 209°–215°.

EXAMPLE 5

1-Substituted 4-(3,4-Dimethoxyphenyl)-2-pyrrolidones

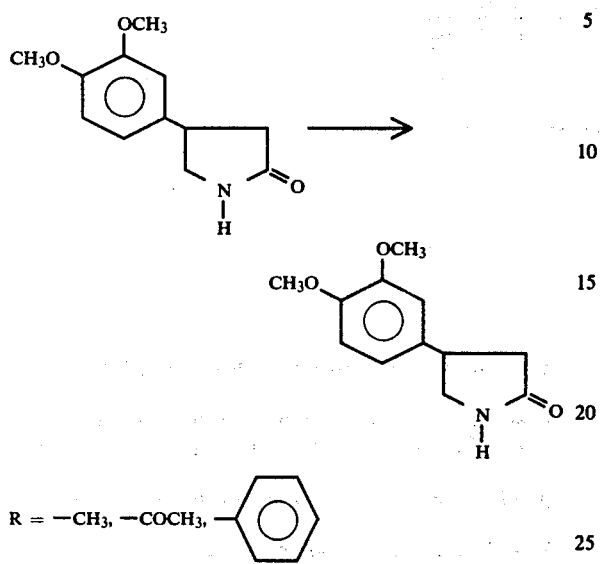

R = —CH₃, —COCH₃, —⟨phenyl⟩

(a) 4-(3,4-Dimethoxyphenyl)-1-methyl-2-pyrrolidone 2.21 g. of 4-(3,4-dimethoxyphenyl)-2-pyrrolidone (10 mmol) is dissolved in 15 ml. of dimethylformamide, combined under ice cooling with 530 mg. of a 50% sodium hydride—paraffin suspension (11 mmol), and gradually heated to 60° under agitation. After the evolution of hydrogen has ceased, 1.56 g. of methyl iodide (11 mmol) in 5 ml. of dimethylformamide is added dropwise at 0° and the mixture heated for 15 minutes to 50°. Thereafter, the mixture is poured into water, worked up as usual with ethyl acetate, and the product thus obtained is 1.3 g. of 4-(3,4-dimethoxyphenyl)-1-methyl-2-pyrrolidone (55% of theory); m.p. 69° (diisopropyl ether).

(b) 1-Acetyl-4-(3,4-dimethoxyphenyl)-2-pyrrolidone

With the use of 0.86 g. of acetyl chloride (11 mmol) in place of the methyl iodide, 1-acetyl-4-(3,4-dimethoxyphenyl)-2-pyrrolidone is obtained analogously to method (a). Yield: 1.4 g. (53% of theory); m.p. 135° (ethanol).

(c) 4-(3,4-Dimethoxyphenyl)-1-phenyl-2-pyrrolidone 2.21 g. of 4-(3,4-dimethoxyphenyl)-2-pyrrolidone (10 mmol), 3.5 g. of iodobenzene (17 mmol), 1.44 g. of potassium carbonate (10.4 mmol), and 100 mg. of pulverized copper are heated for 2 hours to 180°. The mixture is worked up as usual with ethyl acetate, yielding 2.2 g. of 4-(3,4-dimethoxyphenyl)-1-phenyl-2-pyrrolidone (74% of theory); m.p. 104° (ethyl acetate/diisopropyl ether).

(d) 4-(3,4-Dimethoxyphenyl)-2-pyrrolidone-1-acetamide

Analogously to 5(a), but with 5 ml. of hexamethylphosphoric triamide as the solvent, the sodium salt of 4-(3,4-dimethoxyphenyl)-2-pyrrolidone is prepared; this product is combined with 0.94 g. of chloroacetamide (10 mmol) at 0°. The reaction mixture is heated for 4 hours to 70°–90°, cooled, diluted with water, and worked up as usual with ethyl acetate, including an extraction with 2 N sodium hydroxide solution. Yield: 0.64 g. (23% of theory); m.p. 162° (ethanol/DIP).

EXAMPLE 6

4-(3,4-Dimethoxyphenyl)-pyrrolidine-2-thione

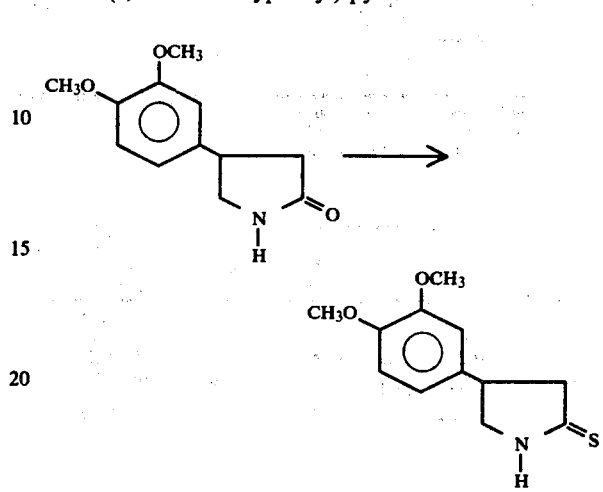

1.98 g. of 4-(3,4-dimethoxyphenyl)-2-pyrrolidone (9 mmol) and 5.4 g. of phosphorus pentasulfide (5.4 mmol) are suspended in a mixture of 9 ml. of acetonitrile and 9 ml. of glycol dimethyl ether. At room temperature and under agitation, 1.4 g. of sodium bicarbonate (18 mmol) is added thereto in small portions. While stirring for another 1.5 hours, the suspension is first dissolved, and shortly thereafter the desired 4-(3,4-dimethoxyphenyl)-pyrrolidine-2-thione is crystallized. The reaction mixture is poured into ice water and vacuum-filtered.

Yield: 1.57 g. (78% of theory); m.p. 151°–152° (ethanol).

Analogously, the following compounds are produced: 4-(3-isobutoxy-4-methoxyphenyl)-pyrrolidine-2-thione (6 a) and 4-(3-cyclopentyloxy-4-methoxyphenyl)-pyrrolidine-2-thione (6 b).

| R | Yield (% of Theory) | Melting Point (Recrystallizing Agent) |
|---|---|---|
| 6 a —CH₂—CH(CH₃)₂ | 68 | 102–104° (ethanol/W) |
| 6 b cyclopentyl | 42 | 109–111° (ethanol/W) |

EXAMPLE 7

A homogeneous mixture is prepared from the following components:

| | | |
|---|---|---|
| 20 | mg. | 4-(3,4-dimethoxyphenyl)-2-pyrrolidone |
| 65.5 | mg. | lactose |
| 32.2 | mg. | corn starch |
| 2.0 | mg. | poly-N-vinylpyrrolidone |
| 0.3 | mg. | magnesium stearate |
| 120.0 | mg. | | and this mixture is compressed, without previous granulation, to tablets with a breaking notch, weighing 120 mg.

EXAMPLE 8

Analogously to Example 7, the following mixture:

| | | |
|---|---|---|
| 5 | mg. | 4-(3-cyclopentyloxy-4-methoxyphenyl)-2-pyrrolidone |
| 105 | mg. | lactose |
| 8 | mg. | corn starch |
| 0.5 | mg. | magnesium stearate |
| 0.5 | mg. | "Aerosil" |
| 1.0 | mg. | talc |
| 120.0 | mg. | | is compressed to tablets having a final weight of 120 mg.

EXAMPLE 9

5 mg. of 4-(3-isobutoxy-4-methoxyphenyl)-2-pyrrolidone is dissolved in 2 ml. of castor oil/benzyl benzoate (4:6). This oily solution is intended for injection.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. 4-(polyalkoxyphenyl)-2-pyrrolidones of the formula

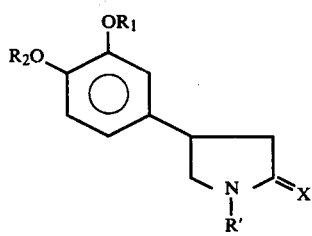

selected from the group consisting of
4-(3-ethoxy-4-metoxyphenyl)-2-pyrrolidone;
4-(3-propoxy-4-methoxyphenyl)-2-pyrrolidone;
4-(3-butoxy-4-methoxyphenyl)-2-pyrrolidone;
4-(3-hexyloxy-4-methoxyphenyl)-2-pyrrolidone;
4-(3-isopropoxy-4-methoxyphenyl)-2-pyrrolidone;
4-(3-(1-methylpropoxy)-4-methoxyphenyl)-2-pyrrolidone;
4-(3-isobutoxy-4-methoxyphenyl)-2-pyrrolidione;
4-(3-allyloxy-4-methoxyphenyl)-2-pyrrolidone;
4-(3-(3-methyl-2-butenyloxy)-4-methoxyphenyl)-2-pyrrolidone;
4-(3-methoxymethoxy-4-methoxyphenyl)-2-pyrrolidone;
4-(3-(2-hydroxyethoxy)-4-methoxyphenyl)-2-pyrrolidone;
4-(3-(2,2,2-trifluoroethoxy)-4-methoxyphenyl)-2-pyrrolidone;
4-(3-benzyloxy-4-methoxyphenyl)-2-pyrrolidone;
4-(3-phenoxy-4-methoxyphenyl)-2-pyrrolidone;
4-(3-methoxy-4-ethoxyphenyl)-2-pyrrolidone;
4-(3-methoxy-4-butoxyphenyl)-2-pyrrolidone;
1-acetyl-4-(3,4-dimethoxyphenyl)-2-pyrrolidone;
4-(3-decyloxy-4-methoxyphenyl)-2-pyrrolidone;
4-83-octadecyloxy-4-methoxyphenyl)-2-pyrrolidone;
4-(3-(2-methylbutyl)-oxy-4-methoxyphenyl)-2-pyrrolidone;
4-(3-neopentyloxy-4-methoxyphenyl)-2-pyrrolidone;
4-(3-isopentyloxy-4-methoxyphenyl)-2-pyrrolidone;
4-(3-(2-propinyl)-oxy-4-methoxyphenyl)-2-pyrrolidone;
4-(3-cyanomethyloxy-4-methoxyphenyl)-2-pyrrolidone;
4-(3-cyclobutoxy-4-methoxyphenyl)-2-pyrrolidone;
4-(3-cyclopentyloxy-4-methoxyphenyl)-2-pyrrolidone;
4-(3-cyclohexyloxy-4-methoxyphenyl)-2-pyrrolidone;
4-(3-(3-methylcyclopentyl)-oxy-4-methoxyphenyl)-2-pyrrolidone;
4-(3-(2-methylcyclopentyl)-oxy-4-methoxyphenyl)-2-pyrrolidone;
4-(3-(3-tetrahydrothienyl)-oxy-4-methoxyphenyl)-2-pyrrolidone;
4-(3-(3-tetrahydrofuryl)-oxy-4-methoxyphenyl)-2-pyrrolidone;
4-(3-cyclopropylmethyloxy-4-methoxyphenyl)-2-pyrrolidone;
4-(3-cyclopentylmethyloxy-4-methoxyphenyl)-2-pyrrolidone;
4-(3-methallyloxy-4-methoxyphenyl)-2-pyrrolidone;
4-(4-propinyloxy-3-methoxyphenyl)-2-pyrrolidone;
4-(4-cyclopentyloxy-3-methoxyphenyl)-2-pyrrolidone;
4-(3,4-diethoxyphenyl)-2-pyrrolidone;
4-(3,4-diisobutoxyphenyl)-2-pyrrolidone;
4-(3-isobutoxy-4-methoxyphenyl)-pyrrolidine-2-thione;
4-(3-cyclopentyloxy-4-methoxyphenyl)-pyrrolidine-2-thione; and
4-(3-(2-tetrahydrofuryloxy)-4-methoxyphenyl)-2-pyrrolidone.

2. The compound of claim 1, 4-(3,4-diisobutoxyphenyl)-2-pyrrolidone.

3. The compound of claim 1, 4-(3-isobutoxy-4-methoxyphenyl)-pyrrolidine-2-thione.

4. The compound of claim 1, 4-(3-cyclopentyloxy-4-methoxyphenyl)-pyrrolidine-2-thione.

5. The compound of claim 1, 4-(3-[2-tetrahydrofuryloxy]-4-methoxyphenyl)-2-pyrrolidone.

6. 4-(polyalkoxyphenyl)-2-pyrrolidones of the formula

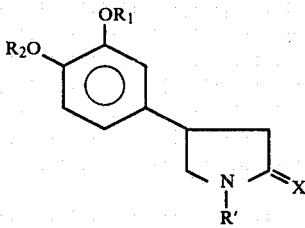

wherein $R_1$ is methyl; $R_2$ is cycloalkyl or cycloalkylalkyl of 3-7 carbon atoms; R' is a hydrogen atom, alkyl of 1-5 carbon atoms, hydrocarbon aryl or aralkyl of up to 10 carbon atoms or alkanoyl of 1-6 carbon atoms; and X is an oxygen atom or a sulfur atom.

7. The compound of claim 1, 4-(3-ethoxy-4-methoxyphenyl)-2-pyrrolidone.
8. The compound of claim 1, 4-(3-propoxy-4-methoxyphenyl)-2-pyrrolidone.
9. The compound of claim 1, 4-(3-butoxy-4-methoxyphenyl)-2-pyrrolidone.
10. The compound of claim 1, 4-(3-hexyloxy-4-methoxyphenyl)-2-pyrrolidone.
11. The compound of claim 1, 4-(3-isopropoxy-4-methoxyphenyl)-2-pyrrolidone.
12. The compound of claim 1, 4-83-[1-methypropoxy]-4-methoxyphenyl)-2-pyrrolidone.
13. The compound of claim 1, 4-(3-isobutoxy-4-methoxyphenyl)-2-pyrrolidone.
14. The compound of claim 1, 4-(3-allyloxy-4-methoxyphenyl)-2-pyrrolidone.
15. The compound of claim 1, 4-83-[3-methyl-2-butenyloxy]-4-methoxyphenyl)-2-pyrrolidone.
16. The compound of claim 1, 4-(3-methoxymethoxy-4-methoxyphenyl)-2-pyrrolidone.
17. The compound of claim 1, 4-(3-[2-hydroxyethoxy]-4-methoxyphenyl)-2-pyrrolidone.
18. The compound of claim 1, 4-(3-[2,2,2-trifluoroethoxy]-4-methoxyphenyl)-2-pyrrolidone.
19. The compound of claim 1, 4-(3-benzyloxy-4-methoxyphenyl)-2-pyrrolidone.
20. The compound of claim 1, 4-(3-phenoxy-4-methoxyphenyl)-2-pyrrolidone.
21. The compound of claim 1, 4-(3-methoxy-4-ethoxyphenyl)-2-pyrrolidone.
22. The compound of claim 1, 4-(3-methoxy-4-butoxyphenyl)-2-pyrrolidone.
23. The compound of claim 1, 1-acetyl-4-(3,4-dimethoxyphenyl)-2-pyrrolidone.
24. 4-(polyalkoxyphenyl)-2-pyrrolidones of the formula

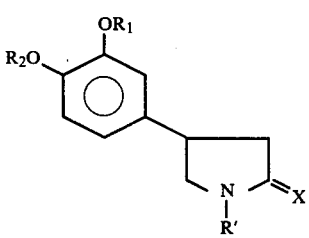

wherein one of $R_1$ and $R_2$ is methyl and the other is mono-, di- or trihaloalkyl; R' is a hydrogen atom, alkyl of 1-5 carbon atoms, hydrocarbon aryl or aralkyl of up to 10 carbon atoms or alkanoyl of 1-6 carbon atoms; and X is an oxygen atom or a sulfur atom.

25. The compound of claim 1, 4-(3-decyloxy-4-methoxyphenyl)-2-pyrrolidone.
26. The compound of claim 1, 4-(3-octadecyloxy-4-methoxyphenyl)-2-pyrrolidone.
27. The compound of claim 1, 4-(3-[2-methylbutyl]-oxy-4-methoxyphenyl)-2-pyrrolidone.
28. The compound of claim 1, 4-(3-neopentyloxy-4-methoxyphenyl)-2-pyrrolidone.
29. The compound of claim 1, 4-(3-isopentyloxy-4-methoxyphenyl)-2-pyrrolidone.
30. The compound of claim 1, 4-(3-[2-propinyl]-oxy-4-methoxyphenyl)-2-pyrrolidone.
31. The compound of claim 1, 4-(3-cyanomethyloxy-4-methoxyphenyl)-2-pyrrolidone.
32. The compound of claim 1, 4-(3-cyclobutoxy-4-methoxyphenyl)-2-pyrrolidone.
33. The compound of claim 1, 4-(3-cyclopentyloxy-4-methoxyphenyl)-2-pyrrolidone.
34. The compound of claim 1, 4-(3-cyclohexyloxy-4-methoxyphenyl)-2-pyrrolidone.
35. The compound of claim 1, 4-(3-[3-methylcyclopentyl]-oxy-4-methoxyphenyl)-2-pyrrolidone.
36. The compound of claim 1, 4-(3-[2-methylcyclopentyl]-oxy-4-methoxyphenyl)-2-pyrrolidone.
37. The compound of claim 1, 4-(3-[3-tetrahydrothienyl]-oxy-4-methoxyphenyl)-2-pyrrolidone.
38. The compound of claim 1, 4-(3-[3-tetrahydrofuryl]-oxy-4-methoxyphenyl)-2-pyrrolidone.
39. The compound of claim 1, 4-(3-cyclopropylmethyloxy-4-methoxyphenyl)-2-pyrrolidone.
40. The compound of claim 1, 4-(3-cyclopentylmethyloxy-4-methoxyphenyl)-2-pyrrolidone.
41. The compound of claim 1, 4-(3-methallyloxy-4-methoxyphenyl)-2-pyrrolidone.
42. The compound of claim 1, 4-(4-propinyloxy-3-methoxyphenyl)-2-pyrrolidone.
43. The compound of claim 1, 4-(4-cyclopentyloxy-3-methoxyphenyl)-2-pyrrolidone.
44. The compound of claim 1, 4-(3,4-diethoxyphenyl)-2-pyrrolidone.
45. 4-(polyalkoxyphenyl)-2-pyrrolidones of the formula

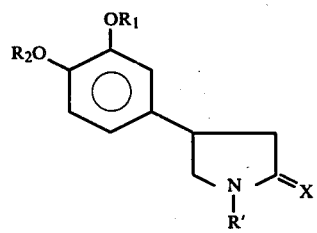

wherein one of $R_1$ and $R_2$ is methyl and the other is tetrahydrothienyl or tetrahydrofuryl; R' is a hydrogen atom, alkyl of 1-5 carbon atoms, hydrocarbon aryl or aralkyl of up to 10 carbon atoms or alkanoyl of 1-6 carbon atoms; and X is an oxygen atom or a sulfur atom.

* * * * *